(12) United States Patent
Blanckaert et al.

(10) Patent No.: US 11,844,581 B2
(45) Date of Patent: Dec. 19, 2023

(54) TOOL WITH TORQUE-ACTUATED END EFFECTOR

(71) Applicant: Steerable Instruments NV, Sint-Denijs-Westrem (BE)

(72) Inventors: Bart Blanckaert, Eeklo (BE); Cyriel Mabilde, Oudenaarde (BE); Frank Dewaele, De Pinte (BE)

(73) Assignee: Steerable Instruments NV, Sint-Denijs-Westrem (BE)

(*) Notice: Subject to any disclaimer, the term of this patent is extended or adjusted under 35 U.S.C. 154(b) by 572 days.

(21) Appl. No.: 17/059,609

(22) PCT Filed: May 27, 2019

(86) PCT No.: PCT/EP2019/063687
§ 371 (c)(1),
(2) Date: Nov. 30, 2020

(87) PCT Pub. No.: WO2019/229002
PCT Pub. Date: Dec. 5, 2019

(65) Prior Publication Data
US 2021/0196409 A1 Jul. 1, 2021

(30) Foreign Application Priority Data

Jun. 1, 2018 (EP) .................................... 18175585

(51) Int. Cl.
*A61B 34/30* (2016.01)
*B25J 9/10* (2006.01)
*B25J 9/16* (2006.01)

(52) U.S. Cl.
CPC ............... *A61B 34/30* (2016.02); *B25J 9/102* (2013.01); *B25J 9/1633* (2013.01); *A61B 2034/301* (2016.02)

(58) Field of Classification Search
CPC ......... F16H 25/06; H02K 7/116; Y10T 74/19; B25J 17/02; B25J 18/06; A61B 34/35;
(Continued)

(56) References Cited

U.S. PATENT DOCUMENTS

| 3,468,175 A | * | 9/1969 | Rabek | ..................... F16H 25/06 74/110 |
| 5,646,466 A | * | 7/1997 | Noji | ....................... H02K 16/00 310/112 |
| 2011/0031829 A1 | | 2/2011 | Bayer | |
| 2012/0074820 A1 | * | 3/2012 | Takeuchi | ............... H02K 29/08 310/75 R |
| 2012/0150154 A1 | | 6/2012 | Brisson et al. | |
| 2017/0367782 A1 | * | 12/2017 | Schuh | .................. A61B 1/0016 |

(Continued)

FOREIGN PATENT DOCUMENTS

| DE | 1963227 U | 6/1967 |
| EP | 3321048 A1 | 5/2018 |

(Continued)

OTHER PUBLICATIONS

International Search Report dated Sep. 9, 2019 from PCT Intl. Appln. PCT/EP2019/063687.

(Continued)

*Primary Examiner* — Nathaniel C Chukwurah
(74) *Attorney, Agent, or Firm* — Amster, Rothstein & Ebenstein LLP

(57) ABSTRACT

Provided is a system comprising a tool (50) and a stator unit (500). The tool (50) comprises an instrument (100, 102) having a proximal end (20) and a distal (40) end, an end effector (300) at the distal end (40) actuated by torque, and a rotor unit (400) body (410) having at least two cammed surfaces to provide the torque. The stator unit (500) comprises a plurality of stator pushers (530-Ua, 530-Va, 530-Wa, 530-Ub, 530-Vb, 530-Wb, 530-Uc, 530-Vc, 530-Wc) configured for movement in a direction radial to a centre of rotation (405) of the body (410) of the rotor unit (400) and (Continued)

for the application of the radial force, whereby movement of the stator pushers induces rotation of the body (410) around the axis of rotation (210).

15 Claims, 8 Drawing Sheets

(58) Field of Classification Search
CPC ......... A61B 17/29; A61B 34/71; A61B 34/37; A61B 2017/00039; A61B 2017/00398; A61B 2017/00477; A61B 2090/571; A61B 2017/2932; A61B 2034/305; A61B 2034/301; A61B 2017/00199; A61B 2017/00212; A61B 2017/2929; A61B 34/30
See application file for complete search history.

(56) References Cited

U.S. PATENT DOCUMENTS

| | | | |
|---|---|---|---|
| 2018/0161111 A1* | 6/2018 | Overmyer | A61B 34/73 |
| 2018/0214226 A1 | 8/2018 | Kan | |
| 2019/0175287 A1* | 6/2019 | Hill | A61B 1/00149 |

FOREIGN PATENT DOCUMENTS

| | | |
|---|---|---|
| WO | 2009071228 A1 | 6/2009 |
| WO | 2009091497 A2 | 7/2009 |
| WO | 2012068156 A2 | 5/2012 |

OTHER PUBLICATIONS

Written Opinion dated Sep. 9, 2019 from PCT Intl. Appln. PCT/EP2019/063687.

\* cited by examiner

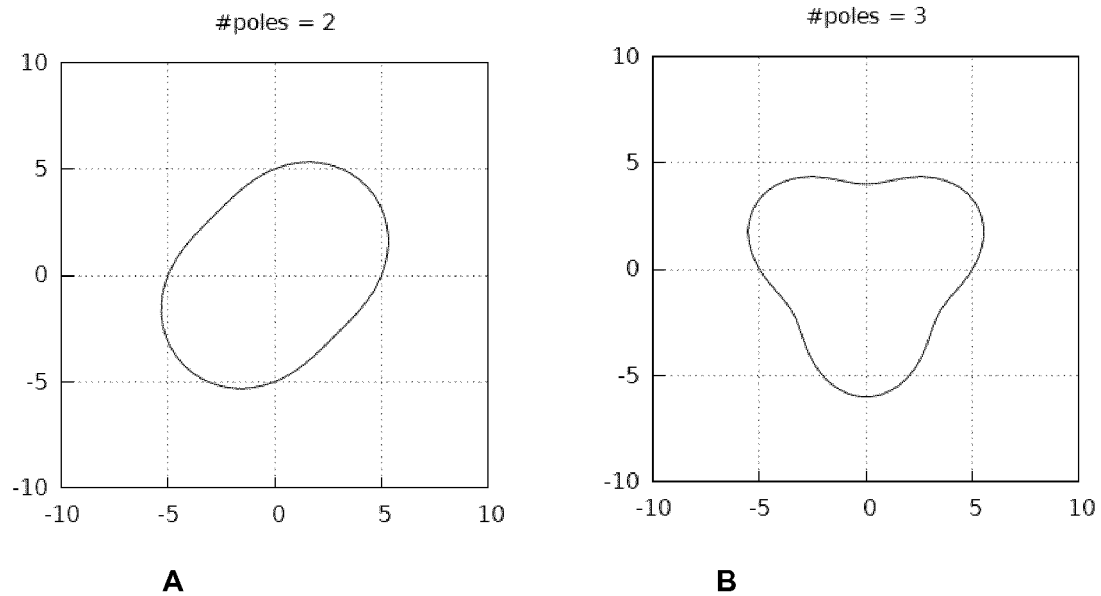
FIG. 10
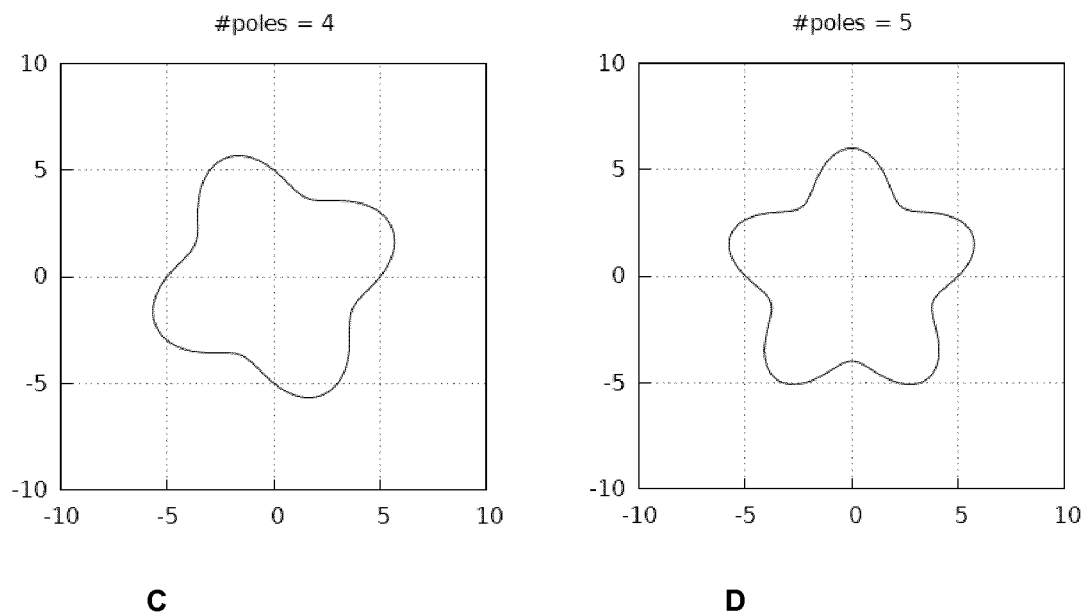

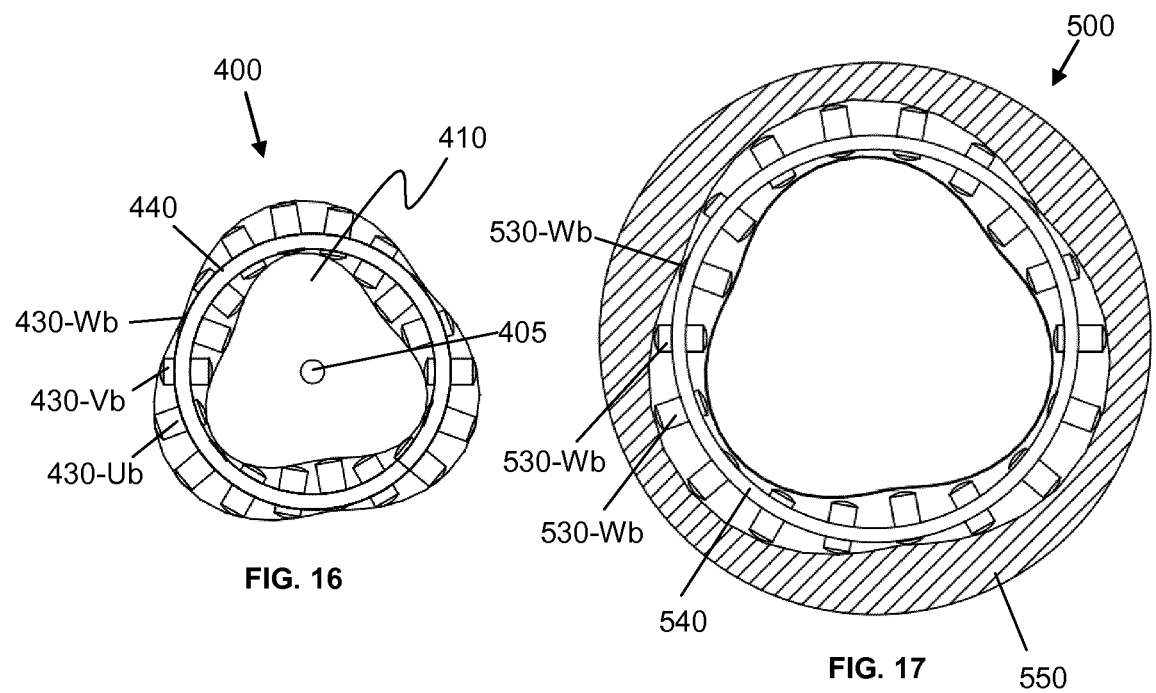
FIG. 16
FIG. 17
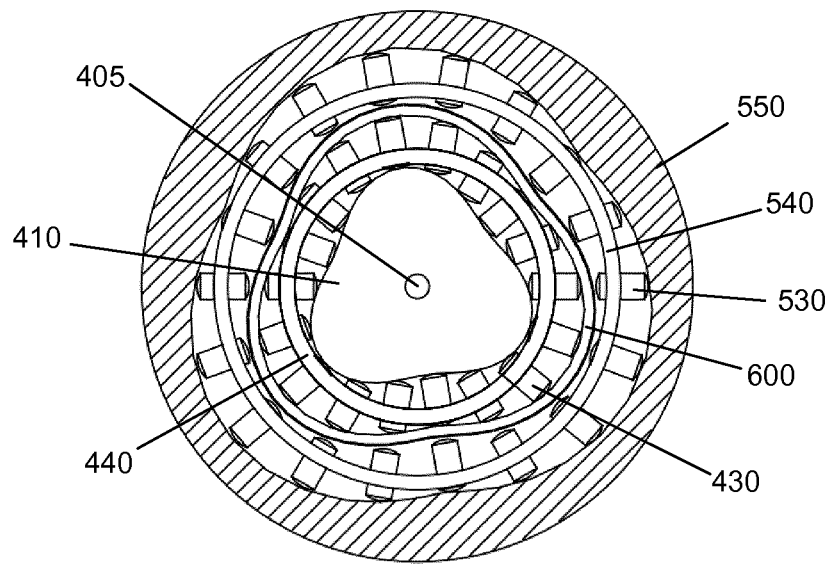
FIG. 18

TOOL WITH TORQUE-ACTUATED END EFFECTOR

CROSS-REFERENCE TO RELATED APPLICATIONS

This application is a U.S. national stage entry under 35 U.S.C. § 371 of PCT International Patent Application No. PCT/EP2019/063687, filed May 27, 2019, which claims priority to European Patent Application No. 18175585.1, filed Jun. 1, 2018, the contents of each of which are incorporated herein by reference in their entirety.

FIELD OF THE INVENTION

The invention is in the field of tools disposed with a torque-actuated end effector for industrial, engineering and medical uses, more in particular for minimally invasive surgery. Most preferably, the tool comprises a steerable instrument, optionally is robotically controllable.

BACKGROUND TO THE INVENTION

A tool such as a surgical instrument with a rotating actuation, for example the leadscrew system in a stapler, needs to be releasably coupled to a surgical system such as a robot-arm or manual handle, specifically flange of a robot arm. In such as system, torque needs to be supplied to the proximal end of the tool so as to actuate the end effector.

In a surgical setting, sterilisation requirements are to be followed. Often the "robot-arm" can only be partially cleaned but and cannot be sterilised. The tool must be and is sterilised. Mostly the sterilised instrument is brought in the operating theatre in a package. Once the sterilised instrument is taken out of its protective package, any contact to potentially contaminated objects needs to be avoided.

It is therefore undesired to connect the sterile instrument to the robot flange as is. A solution known in the art is to cover the robot arm in a sterile drape. This drape implements a sterile barrier. It is typically a polymeric sheet.

It is a problem in the art of how to transmit torque through the sterile barrier without risk of damaging the barrier by twisting as the components rotate, and which avoids providing expensive mechanical joint in a wall of the drape.

SUMMARY

Provided is a system comprising:
a tool (50) comprising:
  an instrument (100, 102) having a proximal end (20) and a distal (40) end comprising a shaft (130), the instrument (100, 102) provided with an end effector (300) at the distal end (40) actuated by torque,
  a drive shaft (402), at least partially flexible for transfer of torque from the proximal end (20) to the end effector (300), disposed in a lumen of the instrument (100),
  a rotor unit (400) comprising a body (410) disposed at the proximal end (20) of the instrument (100, 102) connected to the drive shaft (402), and that rotates around an axis of rotation (210) relative to the proximal end (20) of the instrument (100, 102), and
a stator unit (500) configured to induce rotation of the body (410) around the axis of rotation (210), wherein
  the body (410) of the rotor unit (400) is configured for dismountable engagement with a stator unit (500),
  the body (410) of the rotor unit (400) is disposed with at least two cammed regions each configured to receive radial force from the stator unit (500) that induces rotation of the body (410) around the axis of rotation, and
  the stator unit (500) comprises a plurality of stator pushers (530-Ua, 530-Va, 530-Wa, 530-Ub, 530-Vb, 530-Wb, 530-Uc, 530-Vc, 530-Wc) configured for movement in a direction radial to a centre of rotation (405) of the body (410) of the rotor unit (400) and for the application of the radial force.

The tool may further comprise a connector (110) rotationally fixed in relation to the proximal end of the instrument (100, 102), and the stator unit (500) comprises a complementary fitting, wherein the connector (110) is configured for dismountable attachment of the instrument (100, 102) in fixed relation to the stator unit (500) via the complementary fitting thereon.

The connector (110) may comprise a collar having a polygonal profile.

The rotor unit (400) may further comprise a plurality of rotor pushers (430-Ub, 430-Vb, 430-Wb), each rotor pusher is configured for movement in a direction radial to a centre of rotation of the body (410), and for receiving rotation-inducing force from the stator unit (500) and transferring it to the body (410) as the radial force.

The rotor pushers (430-Ub, 430-Vb, 430-Wb) may be enclosed by a sterile barrier or drape (600).

The instrument (100) may be a steerable instrument (102) comprising a bendable proximal part (120) and a bendable distal part (140) disposed either side of the shaft, the steerable instrument (100) configured such that the bendable distal part (140) bends responsive to bending of the bendable proximal part (120).

The end effector (300) may be attached in fixed rotational relation to the bendable distal part (140) wherein the end effector (300) is axially rotatable when the bendable distal part (140) is in a bent position by a complementary axial rotation of the bendable proximal part (120).

The stator pushers (530-Ua, 530-Va, 530-Wa, 530-Ub, 530-Vb, 530-Wb, 530-Uc, 530-Vc, 530-Wc) may be disposed evenly around a central point, where an axis of movement of the stator pushers coincide.

The stator unit (500) may further comprise a ring cam (550) having an inner surface comprising at least one cammed region, configured such that rotation of the ring cam (550) induces movement of the stator pushers (530-Ua, 530-Va, 530-Wa, 530-Ub, 530-Vb, 530-Wb, 530-Uc, 530-Vc, 530-Wc) for inducing rotation of the body (410) around the axis of rotation (210).

A set of the plurality of stator pushers may be defined as a set of phase-shifted stator pushers, PSSP, wherein the cycles of movement of the pushers within the set of PSSP have that are mutually shifted.

The system may further comprise a robotic arm, and the stator unit (500) may be attached at an effector end of the robotic arm.

The system may further comprise a detachable handle, and the stator unit (500) is integrated into a handle.

Further provided is a tool (50) as defined herein configured for dismountable engagement with a stator unit (500) as defined herein.

Further provided is a stator unit (500) as defined herein configured for dismountable engagement with a tool (50) as defined herein.

Further provided is a use of a tool as defined herein for dismountable engagement with a stator unit (500) as defined herein.

Further provided is a tool (50) comprising:
- an instrument (100, 102) having a proximal end (20) and a distal (40) end comprising a shaft (130), the instrument (100, 102) provided with an end effector (300) at the distal end (40) actuated by torque,
- a drive shaft (402), at least partially flexible for transfer of torque from the proximal end (20) to the end effector (300), disposed in a lumen of the instrument (100),
- a rotor unit (400) comprising a body (410) disposed at the proximal end (20) of the instrument (100, 102) connected to the drive shaft (402), and that rotates relative to the proximal end (20) of the instrument (100, 102),
- wherein body (410) of the rotor unit (400) is configured for dismountable engagement with a stator unit (500), and is configured for rotation around an axis of rotation (210) induced by and relative to the stator unit (500).

The tool may further comprise a connector (110) rotationally fixed in relation to the proximal end of the instrument (100, 102) configured for dismountable attachment of the instrument (100, 102) in fixed relation to the stator unit (500), more in particular to a complementary fitting thereon. The connector (110) may comprise a collar having a polygonal profile configured to engages with a complementary receiving part disposed in relation to the stator (500).

The rotor unit (400) may comprises a rotor of a brushless DC motor. The stator unit (500) may comprise a stator of a brushless DC motor The body (410) of the rotor unit (400) may be disposed with at least two cammed regions each configured to receive radial force from the stator unit (500) that induces rotation of the body (410) around the axis of rotation.

The rotor unit (400) may further comprise a plurality of rotor pushers (430-Ub, 430-Vb, 430-Wb), each rotor pusher is configured for movement in a direction radial to a centre of rotation of the body (410), and for receiving rotation-inducing force from the stator unit (500) and transferring it to the body (410) as the radial force.

The instrument (100) may be a steerable instrument (102) comprising a bendable proximal part (120) and a bendable distal part (140) disposed either side of the shaft, the steerable instrument (100) configured such that the bendable distal part (140) bends responsive to bending of the bendable proximal part (120).

The end effector (300) is attached may be fixed rotational relation to the bendable distal part (140) wherein the end effector (300) is rotatable when the bendable distal part (140) is in a bent position by a complementary rotation of the bendable proximal part (120).

Also provided is a system comprising the tool (50) as described herein, and the stator unit (500) as described herein The stator unit (500) may comprise a plurality of stator pushers (530-Ua, 530-Va, 530-Wa, 530-Ub, 530-Vb, 530-Wb, 530-Uc, 530-Vc, 530-Wc) configured for movement in a direction radial to a centre of rotation (405) of the body (410) of the rotor unit (400) and for the application of the radial force to induce rotation of the body (410).

The stator pushers (530-Ua, 530-Va, 530-Wa, 530-Ub, 530-Vb, 530-Wb, 530-Uc, 530-Vc, 530-Wc) are disposed evenly around a central point, where an axis of movement of the stator pushers coincide.

The stator unit (500) may further comprise a ring cam (550) having an inner surface comprising at least one cammed region, configured such that rotation of the ring cam (550) induces movement of the stator pushers (530-Ua, 530-Va, 530-Wa, 530-Ub, 530-Vb, 530-Wb, 530-Uc, 530-Vc, 530-Wc) for inducing rotation of the body (410) around the axis of rotation (210).

The set of the plurality of stator pushers is defined as a set of phase-shifted stator pushers, PSSP, wherein the cycles of movement of the pushers within the set of PSSP have that are mutually shifted.

The system may further comprise a robotic arm, and the stator unit (500) is attached at an effector end of the robotic arm.

The system may further comprising a detachable handle, and the stator unit (500) integrated into a handle.

FIGURE LEGENDS

FIGS. 10A to D are examples of different cammed regions having a different number of poles (A-2), (B-3), (C-4), (D-5).

Figure 11A:
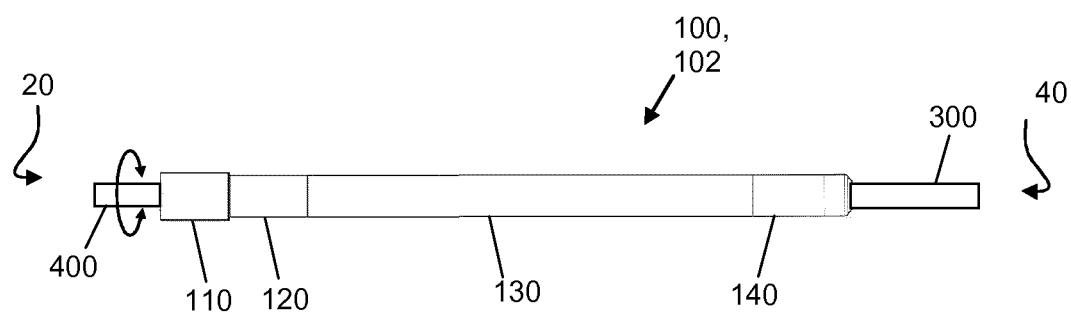

FIG. 11A shows an instrument (100) that is a steerable instrument.

Figure 11B:
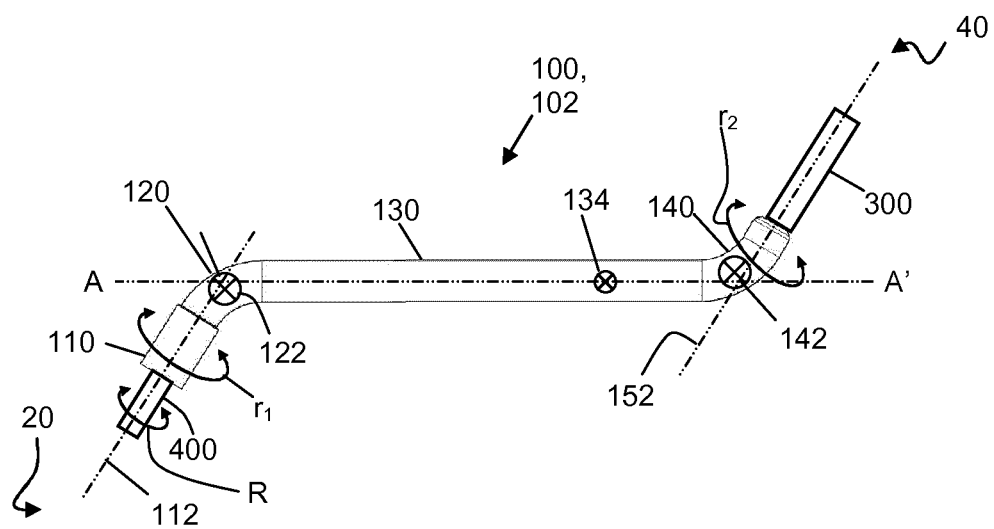

FIG. 11B shows the instrument (100) of FIG. 11 A in a bent configuration.

Figure 12:
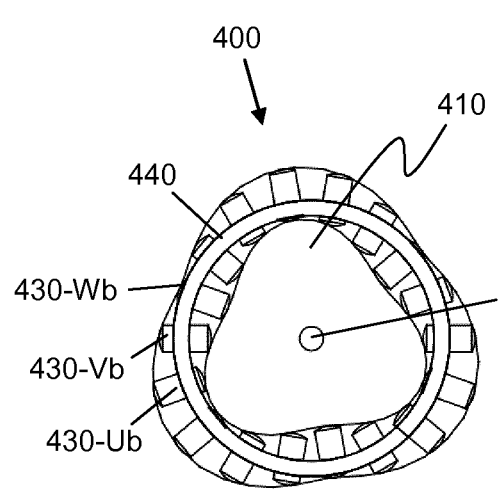

FIG. 11B shows the rotor unit of engaged in a stator unit, where in the stator unit employs a cammed inner ring to apply radial forces to the rotor unit FIG. 12 shows a rotor unit provided with a plurality of rotor pushers.

Figure 13:
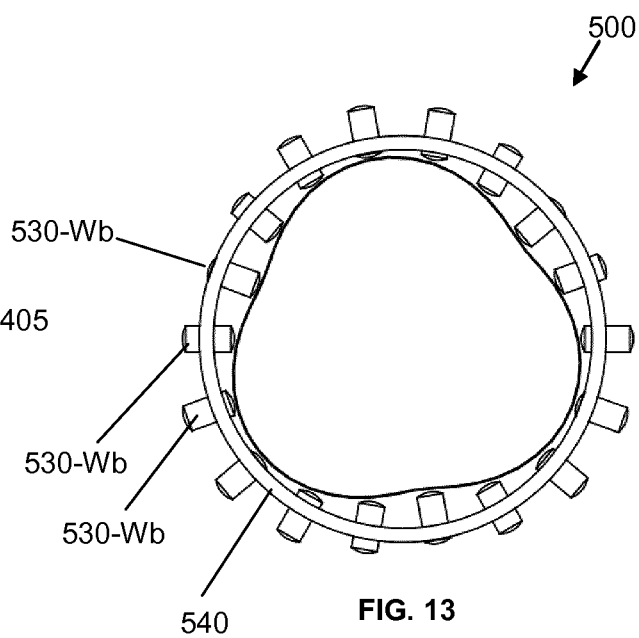

FIG. 13 shows a stator unit provided with a plurality of stator pushers.

Figure 14:
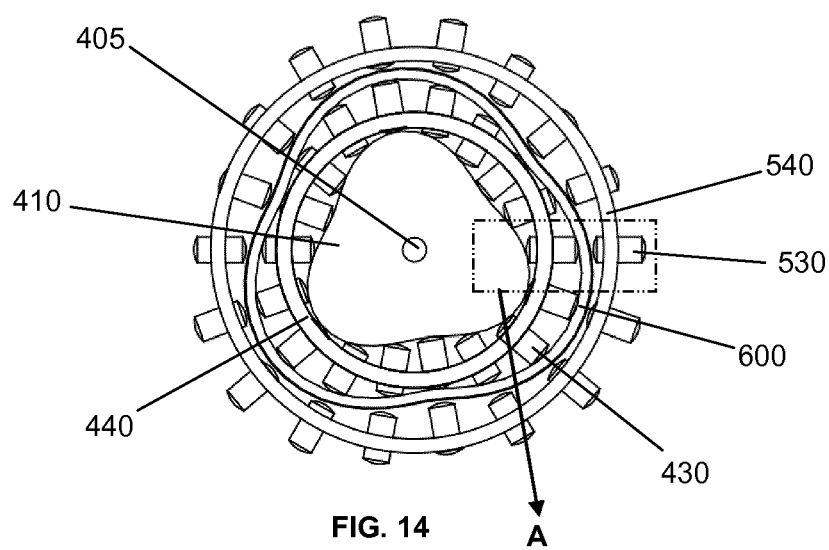

FIG. 14 shows the rotor unit of FIG. 12 engaged in the stator unit of FIG. 13.

Figure 15:
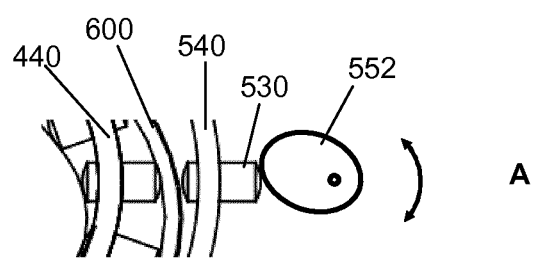

FIG. 15 shows an enlargement of FIG. 14 at box A, wherein the stator pusher is driven by a cammed disc.

FIG. 16 shows a rotor unit provided with a plurality of rotor pushers.

FIG. 17 shows a stator unit provided with a plurality of stator pushers driven by a ring cam.

FIG. 18 shows the rotor unit of FIG. 16 engaged in the stator unit of FIG. 17.

DETAILED DESCRIPTION OF INVENTION

Before the present system and method of the invention are described, it is to be understood that this invention is not limited to particular systems and methods or combinations described, since such systems and methods and combinations may, of course, vary. It is also to be understood that the terminology used herein is not intended to be limiting, since the scope of the present invention will be limited only by the appended claims.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. It will be appreciated that the terms "comprising", "comprises" and "comprised of" as used herein comprise the terms "consisting of", "consists" and "consists of".

The recitation of numerical ranges by endpoints includes all numbers and fractions subsumed within the respective ranges, as well as the recited endpoints.

The term "about" or "approximately" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" or "approximately" refers is itself also specifically, and preferably, disclosed.

Whereas the terms "one or more" or "at least one", such as one or more or at least one member(s) of a group of members, is clear per se, by means of further exemplification, the term encompasses inter alia a reference to any one of said members, or to any two or more of said members, such as, e.g., any 3, NI, 5, >6 or >7 etc. of said members, and up to all said members.

All references cited in the present specification are hereby incorporated by reference in their entirety. In particular, the teachings of all references herein specifically referred to are incorporated by reference.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the appended claims, any of the claimed embodiments can be used in any combination.

In the present description of the invention, reference is made to the accompanying drawings that form a part hereof, and in which are shown by way of illustration only of specific embodiments in which the invention may be practiced. Parenthesized or emboldened reference numerals affixed to respective elements merely exemplify the elements by way of example, with which it is not intended to limit the respective elements. It is to be understood that other embodiments may be utilised and structural or logical changes may be made without departing from the scope of the present invention. The following detailed description, therefore, is not to be taken in a limiting sense, and the scope of the present invention is defined by the appended claims.

The terms "distal" or "distal to" and "proximal" or "proximal to" are used throughout the specification, and are terms generally understood in the field to mean towards (proximal) or away (distal) from the operator's side of an apparatus. Thus, "proximal" or "proximal to" means towards the operator's side and, therefore, away from the workpiece or patient's side. Conversely, "distal" or "distal to" means towards the workpiece or patient's side and, therefore, away from the operator's side. The steerable stapler has a distal and proximal end and components of the stapler including the steerable instrument, stapler head have distal and proximal ends that correspond with distal and proximal ends of the steerable stapler.

In the present description of the invention, reference is made to the accompanying drawings that form a part hereof, and in which are shown by way of illustration only of specific embodiments in which the invention may be practiced. Parenthesized or emboldened reference numerals affixed to respective elements merely exemplify the elements by way of example, with which it is not intended to limit the respective elements. It is to be understood that other embodiments may be utilised and structural or logical changes may be made without departing from the scope of the present invention. The following detailed description, therefore, is not to be taken in a limiting sense, and the scope of the present invention is defined by the appended claims.

Figure 1:
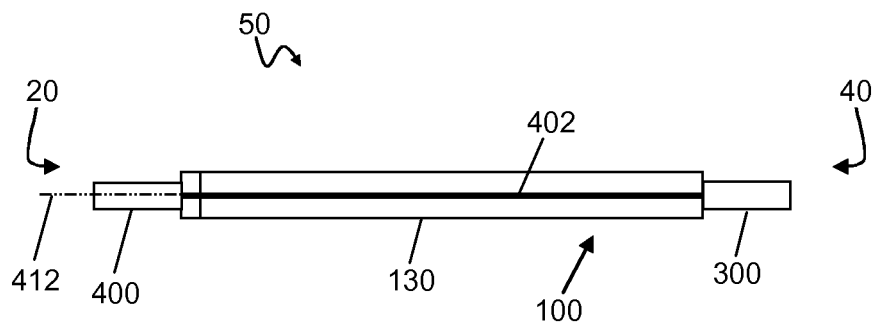
FIG. 1 Depicts a tool as described herein.

Provided herein is a tool (50) comprising an instrument (100) having a proximal end (20) and a distal (40) end as shown, for instance in FIG. 1. The instrument comprises a shaft (130). The instrument (100) is provided with an end effector (300) at the distal end (40) actuated by torque. The tool further comprises a drive shaft (402), at least partially flexible for transfer of torque from the proximal end (20) to the end effector (300), disposed in a lumen of the instrument (100). The tool further comprises a rotor unit (400). The rotor unit (400) comprises a body (410). The rotor unit (400) is disposed at the proximal end (20) of the instrument (100) connected to the drive shaft (402), and in rotates relative to the proximal end (20) of the instrument (100). The proximal end (20) of the instrument (100) hence can remain static while the rotor unit (400) rotates.

The rotor unit (400) is configured for dismountable engagement with a stator unit (500), and the body (410) of rotor unit (400) is configured for rotation around an axis of rotation (210) induced by and relative to the stator unit (500).

The stator unit (500) may be attached to an effector end of a robotic arm. Hence, the position and direction of the shaft may be controllable, and actuation of the end effector (300) from the robotic arm. The stator unit (500) may be integrated into a detachable handle.

The proximal end (20) of the instrument (100) is configured for dismountable attachment in fixed (positional and rotational) relation to a body (510) of the stator unit (500).

The tool (50) may further comprise a connector (110) for dismountable attachment to a fitting disposed in relation to the stator unit (500); the fitting may be provided on the stator unit (500) or on the robotic arm or detachable handle.

With the configuration, there is no or reduced torque, twisting, or pulling force on a sterile barrier provided between the rotor and stator as forces pass through the barrier without locally twisting it.

Figure 3:
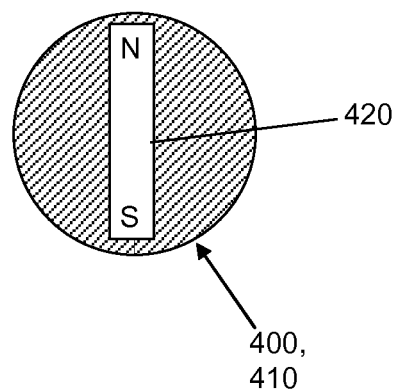
FIG. 3 shows a transverse cross section of a body of a rotor.

The rotor unit (400) may comprise a rotor of a brushless DC motor. The stator unit (500) may comprise a stator of a brushless DC motor, as shown, for instance, in FIGS. 3 and 4. The stator unit (500) may be disposed within an effector end the flange of the robot arm. The rotor unit (400) may be disposed inside the proximal end of the surgical instrument. A body (410) of the rotor unit (400) rotates relative to the proximal end (20) of the instrument (100).

Most brushless electromagnetic DC motors are polyphasic, with an advantage that they can be made to start, regardless the position of the rotor. Electromagnetic motors can be designed with different number of poles. More poles mean that in order to make a full rotation, the electrical field needs to generate more cycles. Typically the rotor will rotate one pair of poles for every electrical cycle. A body (410) of the rotor unit (400) may be fitted with one or more permanent magnets (420) to form a typical brushless DC motor system. A brushless DC motor system is also known as an induction motor system.

The rotor unit may be fitted with short-circuited rotor winding to form an asynchronous induction motor where slip between the stator electrical speed and the rotor mechanical speed causes current to flow in the rotor's short circuited windings, to create a magnetic field. Such induced rotor magnetic field works against the stator field, and cause rotation of the motor.

A brushless DC motor system works well in a broad range of speeds (RPM=0-20 000 RPM). It can be fitted controlled in a so called sensored closed loop system, with a hal sensor position sensing configuration (often, but not limited to hal sensor to sense 3 positions per pole-pair). This position sensing configuration is used by the controller to determine which quadrant the motor is currently in, to supply the correct phase order. BLDC motor can also be controlled in a so called sensored closed loop system. In this system the current and voltage in the different phases is measured. This information is processed and used to know the position and speed of the motor at any time, to be able to supply the correct phase order.

Figure 4:
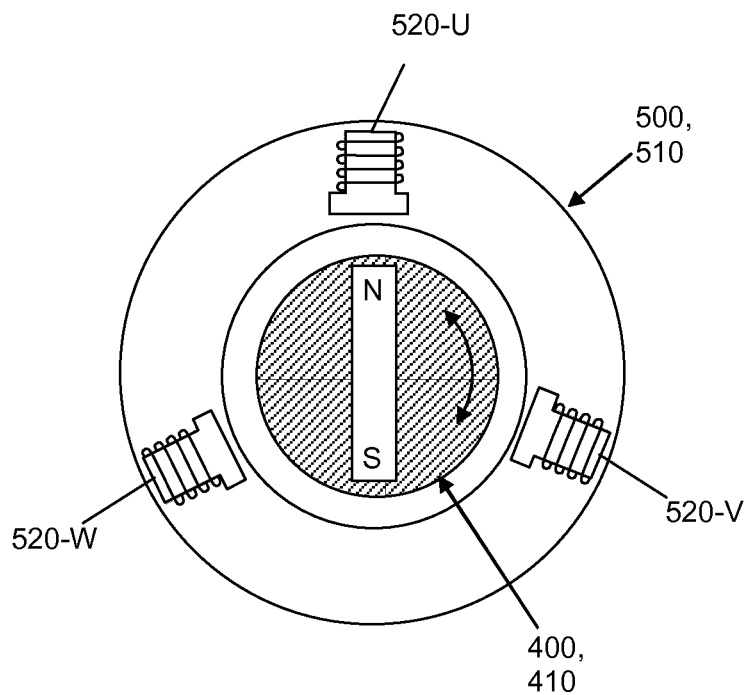
FIG. 4 shows a transverse cross section of a body of a rotor engaged in a stator.
Figure 5:
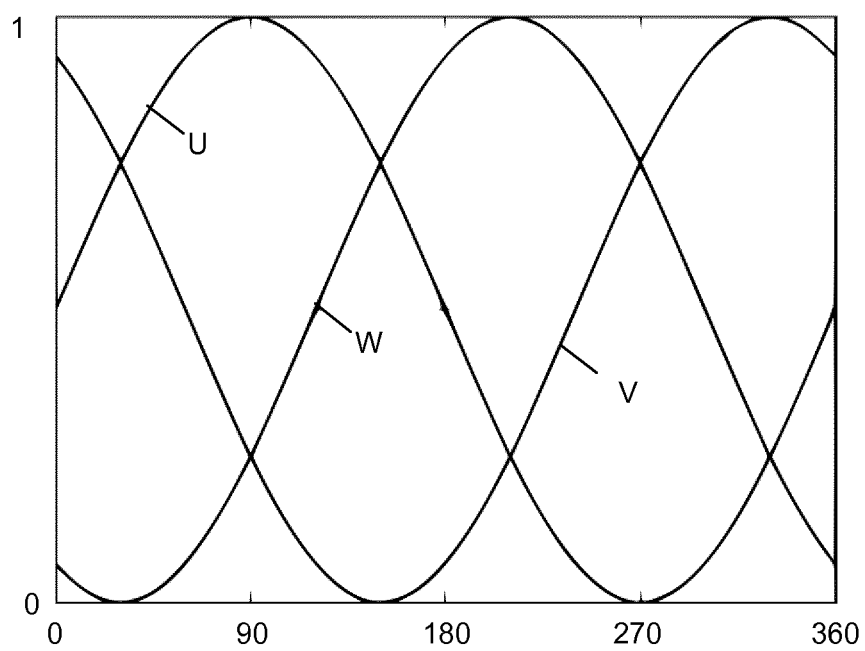
FIG. 5 shows a phase of power to three electromagnets U, V, W having a 120° offset.

An exemplary rotor unit (400) engaged with the stator unit (500) is shown in FIG. 4. It comprises three electromagnets 520-U, 520-V, 520-W that receive 3 phases of 3 phase electric supply. Each phase is 120° offset as shown in FIG. 5. Phases U, V, W are governed by the followed equations:

$$U(t)=A\sin(\omega t)$$

$$V(t)=A\sin(\omega t+2\pi/3)$$

$$W(t)=A\sin(\omega t+4\pi/3)$$

Where A is the amplitude, t is time and ω is angular speed of frequency, The three electromagnets 520-U, 520-V, 520-W induce rotation of the rotor body (410) which contains a permanent magnet disposed in fixed (positional and rotation) relation to the rotor body (410). Typically an induction motor system has a typical designed nominal speed. Different types of drives exist to control the speed of this kind of motor system (V/Hz control, open loop vector control, closed loop vector control).

Figure 6:
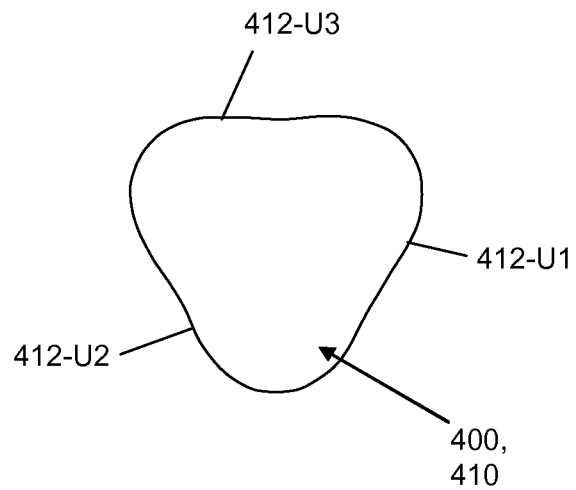
FIG. 6, shows cammed regions arranged circumferentially around the body of the rotor unit.

The body (410) of the rotor unit (400) having an axis of rotation where and edge of the body may be disposed with at least one, preferably at least two cammed regions each configured to receive a radial force from the stator unit (500) that induces rotation of the body (410) around the axis of rotation. As shown in FIG. 6, at least six cammed surfaces (three indicated 412-U1 to 412-U1) are arranged circumferentially around the body (410) of the rotor unit (400).

A cammed region is a contiguous where the radius from a centre of rotation of the body to an edge of the body gradually changes (e.g. moves inwards or outwards) as the body (410) rotates. The change is observed from a fixed radial direction (e.g. 3 o'clock position). The application of a radial force to the cammed surface induces the body to rotate.

The number of cammed regions may be 2, 3, 4, 5, 6 or more. A cammed region (412-U1 to 412-U1) has an axis that co-incides with a centre of rotation of the rotor unit (400) body (410). The cammed region (412-U1 to 412-U1) can rotate about this axis (by bearing, bushing and the like), thereby rotating the body (410). The cammed region is disposed on an edge of the body (410). The cammed region is not circular. The cammed region (412-U1 to 412-U1) may be outside contour. The cammed region (412-U1 to 412-U1) may be outside ridge.

Rotation of the body (410) of the rotor unit (400) may be induced by application of one or more forces in a direction radial to a centre of rotation of the body (410) of the rotor unit (400). As exemplified in FIG. 7, the forces may be provided by a plurality of stator pushers (530-Ua, 530-Va, 530-Wa, 530-Ub, 530-Vb, 530-Wb, 530-Uc, 530-Vc, 530-Wc) disposed in the stator unit (500). Each stator pusher is configured for movement in a direction radial to a centre of rotation of the body (410). The stator pushers (530-Ua, 530-Va, 530-Wa, 530-Ub, 530-Vb, 530-Wb, 530-Uc, 530-Vc, 530-Wc) may be disposed evenly around a central point, the central point being where the axis of movement coincide. The stator pushers (530-Ua, 530-Va, 530-Wa, 530-Ub, 530-Vb, 530-Wb, 530-Uc, 530-Vc, 530-Wc) may move relative to a stator pusher support (540). The stator pusher support (540) is preferably disposed in fixed (rotational and/or positional) relation to a housing of the stator (500).

Figure 7:
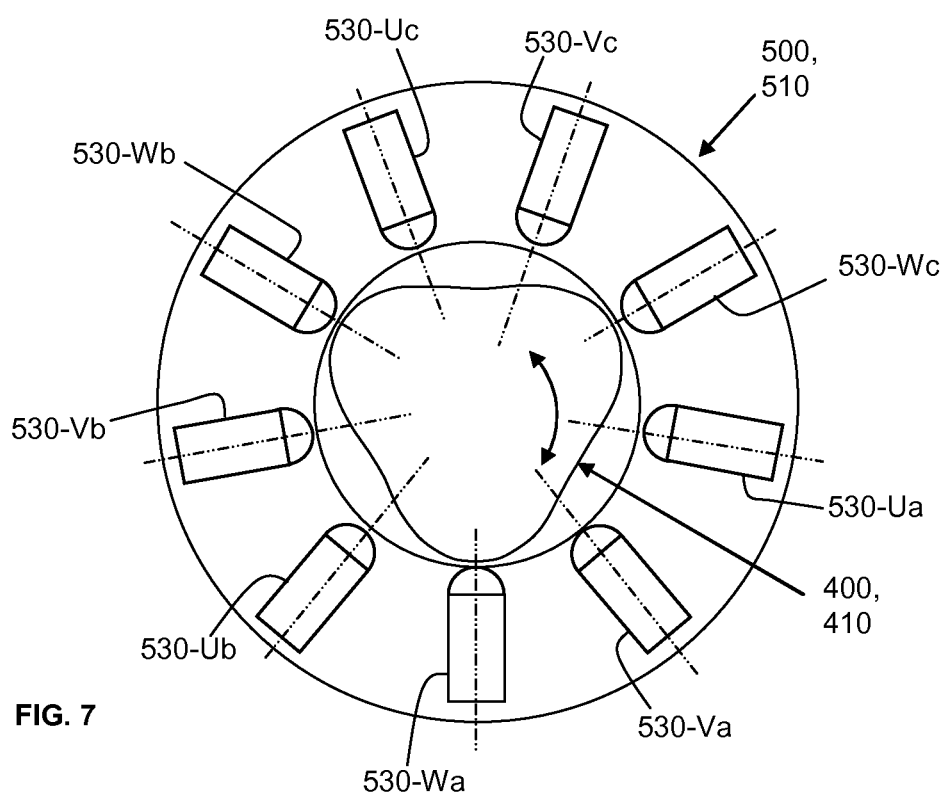
FIG. 7 shows the rotor unit of FIG. 6 engaged in a stator unit, and the stator unit provided with a plurality of pushers (not deployed).
Figure 9:
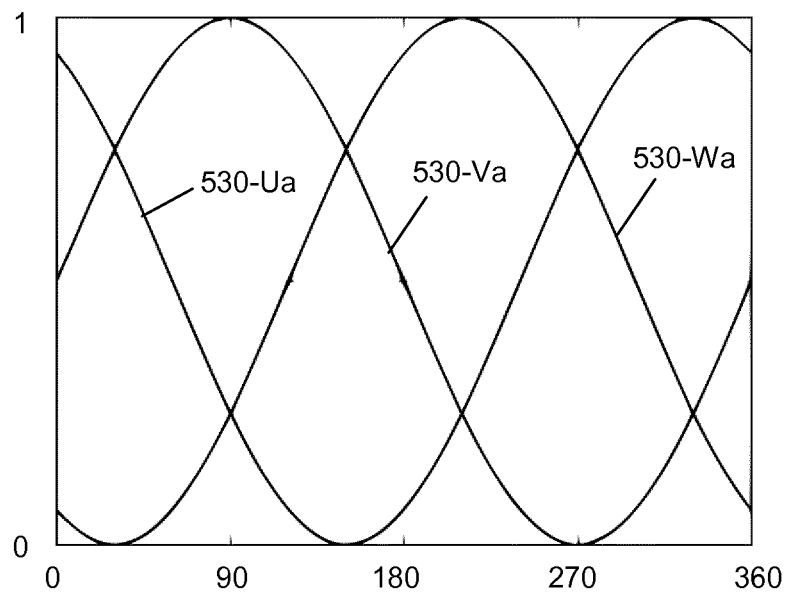
FIG. 9 shows a cycle of force applied by three pushers U, V, W being offset by 120° offset.

A set of the plurality of stator pushers may be defined as a set of phase-shifted stator pushers (PSSPs), wherein an advance and retract movement of each PSSP follows a cycle have a certain phase or frequency, and the phase of each cycle is shifted. In FIG. 7, there are three sets of PSSPs, set 'a' being 530-Ua, 530-Va, 530-Wa, set 'b' being 530-Ub, 530-Vb, 530-Wb and set 'c' being 530-Uc, 530-Vc, 530-Wc. In set 'a' (FIG. 9), a cycle of movement of each pusher 530-Ua, 530-Va, 530-Wa is offset by 120 deg. Radial movement of a 'U' pusher in PSSP set 'a' along the cammed region induces rotation of the body (410) of the rotor unit (400) and aligns the cammed region with the subsequent stator pusher ('V' pusher in PSSP set 'a'). Radial movement of the 'V' pusher in PSSP set 'a' along the cammed region induces further rotation of the body (410) of the rotor unit (400) and aligns the cammed region with the next stator pusher ('W' pusher in set 'a'). Pushers in a set of PSSPs may be arranged together in a segment.

Figure 8:
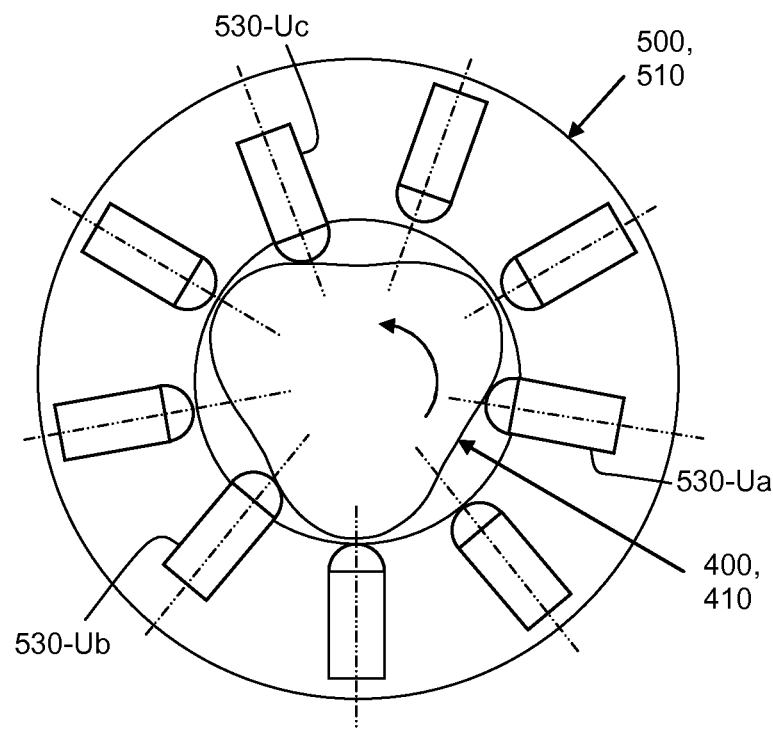
FIG. 8 shows the arrangement of FIG. 7 wherein a group of pushers (U) in deployed.

A set of the plurality of stator pushers may be defined as a set synchronised stator pushers (SYSP), wherein a cycle of movement of each stator pusher within the set of SYSP s is aligned i.e. the phases are fully in-sync. In FIG. 7, there are three set of SYSP s, SYSP set 'U' being 530-Ua, 530-Ub, 530-Uc, SYSP set 'V' being 530-Va, 530-Vb, 530-Vc and SYSP set 'W' being 530-Wa, 530-Wb, 530-Wc. Thus radial forces are applied at the same time by stator pushers in a particular set of SYSP. In FIG. 8, force is applied by the set of SYSP (530-Ua, 530-Ub, 530-Uc) at the same time, thereby rotating the body (410) of the rotor unit (400) anticlockwise.

As exemplified in FIGS. 12 and 16, the rotor unit (400) may further comprise rotor pushers (430-Ub, 430-Vb, 430-Wb) disposed in the rotor unit (400). Each rotor pusher is configured for movement in a direction radial to a centre of rotation of the body (410). The rotor pushers (430-Ub, 430-Vb, 430-Wb) may be disposed evenly around central point (405), the central point being where the axes of movement coincide. The rotor pushers may be passive. The application of a radial force from the stator unit (400) advances the rotor pushers (430-Ub, 430-Vb, 430-Wb) towards the axis of rotation (405) of the rotor unit (400) body (410). The rotor pusher is configured for receiving rotation-inducing force from the stator unit (500) and transferring it to the rotor body (410) as the radial force. The rotor pushers (430-Ub, 430-Vb, 430-Wb) may be arranged in the rotor unit (400) so as to be aligned with the stator pushers (FIGS. 13 and 17, 530-Ub, 530-Vb, 530-Wb) when the rotor unit (400) is engaged with the stator unit (500)—see FIGS. 14 and 18. The rotor pushers (5430-Ub, 430-Vb, 430-Wb) may move relative to a rotor pusher support (440). The rotor pusher support (440) is preferably disposed in fixed (rotational and/or positional) relation to the instrument shaft (130).

In the aligned position, force generated by the stator pushers (530-Ub, 530-Vb, 530-Wb) is transferred to the corresponding rotor pushers (430-Ub, 430-Vb, 430-Wb). When a rotor pusher and stator pusher is aligned, they may be co-axially or non-coaxially aligned. Advantageously, the presence of rotor pushers allows the transfer of purely radial forces without a component of rotation, make it suitable for use with a sterile barrier or drape (600).

A pusher (stator (530) and/or rotor (430)) may be rigid. A pusher may be non-compressible.

A pusher (stator (530) and/or rotor (430)) may be positioned in linear bearings or bushings and may only translate along their axis. A pusher (stator (530) and/or rotor (430)) may be cylindrical; it may be provided with a thread such that rotation rotate about its axis provides movement in a direction radial to a centre of rotation of the body (410) of the rotor unit (400). A pusher (stator (530) and/or rotor (430)) may disposed in a support (stator (540) and/or rotor (440), and moveable relative to the support.

A stator pusher (530-Ua, 530-Va, 530-Wa, 530-Ub, 530-Vb, 530-Wb, 530-Uc, 530-Vc, 530-Wc) is actively driven in stator unit (500). It may be driven by a ring cam (550) as shown for instance in FIGS. 17 and 18. The inner surface of the ring cam (550) contains at least one cammed region that corresponds to the at least one cammed region of the rotor unit (400) body (410). Alternatively, it may be driven by a cammed circular disc (552) as shown, for instance in FIG. 15. Where there are multiple cammed circular discs (552), one for each stator pusher, their rotations may be synchronised by one or more gears, belts, timing belts, or may be driven by individual synchronised servos.

The body (410) of the rotor unit (400) having the cammed region of may be defined as a mechanical system with p poles ($P_1, \ldots Pp$) and n phases ($F_1, \ldots Fn$), giving rise to 2*p cammed regions. The system has n*p pushers (530), which have a (linear) axis of movement. These pushers (530) are radially positioned around an axis of rotation of the body (410) of the rotor unit (400). The axis of movement of the pushers (530) are spread out and the angle between each pusher is 360/(n*p) degrees. The cammed region (412-U1 to 412-U1) may have a shape that has the following mathematical function in polar coordinates (r, θ):

(in polar coordinates, a circle is: r=R))

f(α) is a periodic function with period 360°

A is the amplitude of the actuating wave

R is the mean radius of the rotor unit body (410)

$$r(\theta)=R+(Af(\theta*p))$$

example: $f(\alpha)=\sin(\alpha)$ $$r(\theta)=R+(Af(\theta*p))$$

Examples of different cammed regions is provided in FIG. 10 A to D having a different number of poles and cammed regions (A-2), (B-3), (C-4), (D-5). For every pole (p), n-phases will actuate. In the example of FIG. 7, a 3 pole CAM is actuated by 3 phases: U,V,W.

The instrument (100) may be an engineering tool, industrial tool, or surgical instrument, having use for any type of remote controlled manipulation or working. The instrument (100) may be a surgical instrument, such as, for instance, a minimally invasive surgical instrument, a laparoscopic instrument, and endoscopic instrument, or an endovascular catheter. The instrument (100) may be used in an articulated instrument such as but not limiting to endovascular, endoscopic, neurosurgical, ENT (ear, nose and throat), orthopaedic applications, surgical instruments, robotic tele-operated medical robotics or hand-held surgical tools and industrial applications. The instrument (100) may be a steerable instrument (102) described later below.

The instrument (100, 102) shaft (130) may be rigid or semi-rigid, or may be flexible and become rigid or semi-rigid when co-operating with a rigid or semi-rigid exotube or outer tube, endotube or inner tube. The shaft part is longitudinal, meaning it is longer in one direction. It does necessarily not imply the shaft part is straight. The shaft part may be straight or curved, for instance, having a C- or S-shape. The shaft may be straight. The shaft preferably has a circular transverse (perpendicular to a central axis) profile. Where the instrument (100, 102) is a steerable instrument (102) (see later below) the distal end of the shaft is disposed with the BDP (140) and the proximal end of the shaft is disposed with the BPP (120).

The shaft (130) of the instrument (100, 105) may adopt different directions. The direction of the shaft refers to its angular placement. Changing a direction of the shaft is achieved typically by a pivoted rotation around a fulcrum zone (134). The fulcrum zone coincides with a longitudinal axis (A-A') of the shaft, for instance, a central longitudinal axis of the shaft. Such movements have two degrees of freedom (2-DOF), and may be known as pitch and yaw. When referring to direction, two degrees of freedom is equivalent to a rotation about two axes. The fulcrum zone (134) is where axes of rotation intersect. The fulcrum zone typically coincides with an entry point to the space being investigated, for instance with a hole made in a wall, membrane or port. The fulcrum is provided by the entry point. Where the instrument (100, 105) is a laparoscopic medical instrument, the fulcrum zone is placed at a bodily incision where the laparoscopic medical instrument is introduced. The minimally invasive instrument is typically enters the body via a trocar—a tube-like port inserted into an incision—that supports the steerable instrument and is amendable to pivoted rotation around the fulcrum point of the incision.

The shaft (130) of the instrument (100, 105) may adopt axial positions. The axial position of the shaft refers to its axial (A-A') positional placement. Changing an axial position of the shaft is achieved typically by displacing the shaft axially in a A-A' direction. Such movement has one degree of freedom (1-DOF), and may be known as axial displacement. The entry point to the working space e.g. a bore hole, maintenance port, or a bodily incision supports the steerable instrument and allows the instrument shaft to slide relative to the entry point. Where the steerable instrument is a minimally invasive medical instrument, the medical instrument is introduced via a bodily incision. The medical instrument is typically enters the body via a trocar—a tube-like port inserted into an incision—that supports the steerable instrument and allows the instrument shaft to slide relative to the trocar.

The instrument (100) end effector (300) may comprise any suitable tool for a remotely controlled application, such as a screw driver, abrasive pad, drill bit, gripper, pliers, cutting scissors, stapler, sealer and the like. The instrument (100) end effector (300) may be any tool useful in a surgical procedure, tasks as gripper, pliers, cutting scissors, stapler, drill and the like.

The term end effector (300) also includes a coupling for attachment to a tool such as mentioned above. The coupling may be rotationally fixed in relation to the BDP, and the coupling is rotatable when the BDP is in a bent position, by a complementary rotation of the BPP. A tool mounted to the coupling is rotationally fixed in relation to the BDP.

Rotationally fixing the coupling or end effector relative to the BDP may be achieved using a permanent (non-adjustable) connection or joint, or by means of a lockable element configured to allow rotational adjustment of and to rotationally fix the coupling or end effector in rotational relation to the BDP.

The instrument (100, 102) may further comprise a connector (110) configured for dismountable attachment of the instrument in relation to the stator unit (500), more in particular to a fitting. The fitting may be provided on the stator unit (500) or on an effector end of the robotic arm.

The connector (110) is rotationally fixed in relation to the proximal end of the instrument (100, 102). The connector (110) is rotationally fixed in relation to the proximal terminal end or tip of the instrument (100, 102). The connector (110) is attached fixed in relation to the proximal terminal end or tip of instrument (100, 102). The connector (110) may be provided attached to the proximal terminal end or tip of the instrument (100, 102).

Rotationally fixing the connector (110) relative to the proximal terminal end or tip of the instrument (100, 102) may be achieved using a permanent (non-adjustable) connection or joint, or by means of a lockable element configured to allow rotational adjustment of and to rotationally fix the connector in rotational relation to the instrument (100, 102).

Where in instrument (100) is a steerable instrument (102) (see later below), the connector (110) is rotationally fixed in relation to the BPP (120). The connector (110) is rotationally fixed in relation to the proximal terminal end or tip of BPP. The connector (110) is attached fixed in relation to the proximal terminal end or tip of BPP. The connector (110) may be provided attached to the proximal terminal end or tip of BPP. The connector (110) may be provided attached to the aforementioned cylindrical portion. Rotationally fixing the connector (110) relative to the BPP proximal terminal end or tip may be achieved using a permanent (non-adjustable) connection or joint, or by means of a lockable element configured to allow rotational adjustment of and to rotationally fix the connector in rotational relation to the BPP.

The connector may have a collar-like form, as shown, for instance, in FIGS. 11A and 11B. It may have a polygonal (e.g. triangular, square, pentagonal, hexagonal profile) profile that engages with a complementary receiving part in the fitting, thereby preventing rotation. The connector (110) t may have another shape, such as L-shape, C-shape, F-shape. The connector may be rigid.

The connector (110) may be configured for dismountable attachment to a complementary fitting on the stator unit (500) or robotic arm or handle. The connector (110) may be configured for non-rotational dismountable attachment to a complementary fitting on the on the stator unit (500) or robotic arm or handle. The connector (110) may be configured for displaceable dismountable attachment to a complementary fitting on the stator unit (500) or robotic arm or handle. The connector (110) may be configured for non-rotational dismountable attachment to a complementary fitting on the stator unit (500) or robotic arm or handle.

It is appreciable that the attachment to the robotic arm is to the effector end of the robotic arm, typically in connection—in a straight line or at an angle—with the end joint.

The end effector is actuatable by means of a drive shaft that is at least partly flexible attached. It is attached at a distal end to the end effector. At the proximal end, the drive shaft is connected to the rotor unit.

The drive shaft may be disposed within a lumen of the instrument. The drive shaft may be disposed in a lumen of the steerable instrument at least in bendable distal part and optionally of the shaft.

At the proximal end, the drive shaft may be directed connected to the rotor unit, or connected via one or more gears, for instance to amplify movement or torque.

The instrument (100) may be a non-steerable instrument i.e. the direction of the end effector (300) is fixed relative to the shaft direction.

The instrument (100) may be a steerable instrument (102) having a proximal end (20) and a distal (40) end comprising a shaft (130), a bendable proximal part (120) and a bendable distal part (140), the steerable instrument (102) configured such that the bendable distal part (140) bends responsive to bending of the bendable proximal part (120) as shown, for instance, in FIGS. 11A and 11B. The bending of the bendable proximal part (120) and of a bendable distal part (140) may be omnidirectional. The end effector (300) may be attached in fixed rotational relation to the bendable distal part (140) wherein the end effector (300) is (axially) rotatable when the bendable distal part (140) is in a bent position by a complementary (axial) rotation of the bendable proximal part (120).

FIG. 11A is an illustration of a tool (50) comprising a steerable instrument (102). It has a proximal end (20) and a distal (40) end. The tool (50) and steerable instrument (102) have a proximal end (20) and a distal (40) end. The steerable instrument (102) comprises a shaft (130), a bendable proximal part, BPP (120) and a bendable distal part, BDP (140). A connector (110) configured for dismountable attachment in relation to the stator unit (500) is attached in fixed rotational relation to the proximal terminal end (20) of the BPP (120). An end effector (300) is attached in fixed rotational relation to the distal terminal end (40) of the BDP (140). The shaft (130) pivots around a fulcrum zone (134). A central axis (132) of the shaft (130), an axis of rotation (112) of the connector (110), and an axis of rotation (152) of the end effector (300) are depicted.

Figure 2:
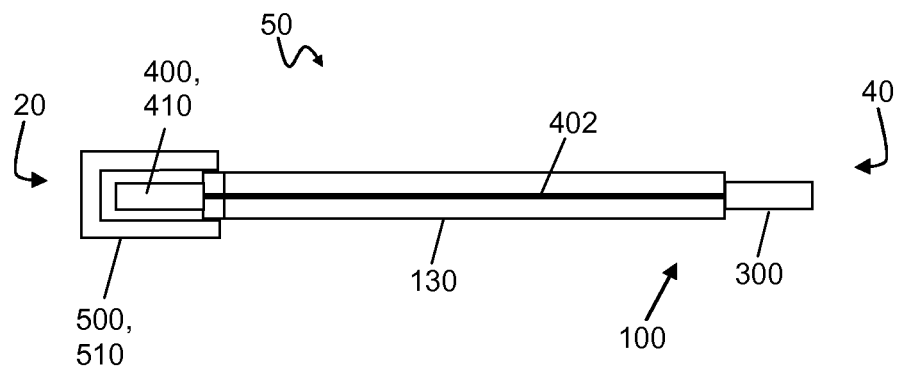
FIG. 2 Depicts a tool as described herein engage with a stator.

FIG. 11B shows the steerable instrument (102) of FIG. 2A wherein the BDP (140) is bent responsive to a bending of the BPP (120), and the direction of the end effector (300) diverges from the direction of the shaft (130)

In FIG. 11A, the BPP (120) and a BDP (140) are straight; an axis of rotation (152) of the end effector (150), a central longitudinal axis (132) of the shaft (130), and an axis of rotation (112) of the connector (110) are mutually coaxial. In FIG. 2B, the BDP (140) is bent responsive to bending of the BPP (120), and the end effector (300) is rotatable around its axis of rotation (152) when the BDP (140) is in a bent position (relative to the shaft) by a complementary rotation of the connector (110) around its axis of rotation (112). Axes of rotation (112) of the BPP (120) at different directions intersect at a zone of motion (122) along the BPP (120). In this figure, the BDP (140) bends along a curve, and not around a revolute joint; axes of rotation (112) of the BDP (140) at different directions intersect at a zone of motion (142) along the BDP (140).

The distal (40) tip or end effector (300) of the steerable instrument (102) can adopt different directions. The direction of the distal tip or end effector (300) refers to its angular placement relative to the shaft (130). Changing a direction of the distal tip or end effector (300) is achieved primarily by actuation of the BPP (120) that changes the direction of BDP (140). A central axis (FIG. 11B, 152) of the distal tip or end effector (300) in different directions intersect at a BDP (140) zone of motion, ZOM, (142) that is a zone coinciding with a central axis (A-A') of the shaft. Bending movements of the BDP (140) has two effective degrees of freedom (2-DOF) around its zone of motion (142), and may be known as effective pitch and effective yaw of the distal tip or end effector (300) that is different from the pitch and yaw of the instrument shaft (130). The geometric centre of the BDP zone of motion (BDP-CZOM) can be used as an effective fulcrum point to robotically control the direction of the distal tip or end effector, even when the BDP (140) bends along a curve. Advantageously, treating the direction of the distal tip or end effector (300) as pivoting around BDP-CZOM allows the axes of rotation of the last 2 or 3 revolute joints of the robotic arm to intersect at the BPP-CZOM, thereby reducing the volume in which the links towards the robotic base move and hence reducing a risk of collision with objects including adjacent equipment and additional robotic arms.

The direction of the connector (110) refers to its angular placement relative to the shaft. Changing a direction of the connector may be achieved by the robotic arm. A central axis (FIG. 11B, 112) of the connector (110) in different directions intersect at a BPP zone of motion (122) that is a zone coinciding with a central axis (A-A') of the shaft. Bending movements of the BPP (120) has two effective degrees of freedom (2-DOF) around its zone of motion, and may be known as effective pitch and effective yaw of the connector (110) that is different from the pitch and yaw of the instrument shaft. The inventors have found that a geometric centre of the BPP zone of motion (BPP-CZOM) can be used as an effective fulcrum point to control the direction of the direction of the connector or handle, even when the BPP bends along a curve. Advantageously, treating bending of the connector (110) as pivoting around BPP-CZOM allows the axes of rotation of the last 2 or 3 revolute joints of the robotic arm to intersect at the BPP-CZOM, thereby reducing the volume in which the robotic links towards the base move and hence reducing a risk of collision with objects including adjacent equipment and additional robotic arms.

The BPP (120) is disposed at a proximal end (20) of the shaft (130). It is axially rotationally fixed to the proximal end (20) of the shaft. The BPP (120) may contact the shaft (130). The BPP (120) may be adjacent to the shaft. Movement of the BPP (120) induces a movement response in the BDP. The BPP may be configured to move omni-directionally i.e. in any radial direction while the shaft is rotationally fixed. BPP is preferably configured to move in any radial direction (about 360° with respect to central longitudinal axis (A'-A) of the shaft part) while the shaft is axially-rotationally fixed. Movement of BPP(120) in different radial directions and to different bending degrees results in a corresponding change in radial direction and/or degree of bending of the BDP. The BPP (120) may comprise a plurality tandemly arranged joints and is configured to bend in a curve. The BPP (120) may be configured to bend around one or more tandemly arranged joints (e.g. ball and socket joints) each having 2 DOF. The BPP (120) may be configured to bend around two or more tandemly arranged joints (e.g. revolute joints offset by 90 deg) each having 1 DOF. The BPP (120) may be configured to bend along a moulded flexible member as disclosed, for instance, in US 2006/0095074. The BPP (120) may be configured to bend along a curve.

The BDP (140) is disposed at a distal end of the shaft. It is axially rotationally fixed to the distal end of the shaft. The BDP (140) may contact the shaft. The BDP (140) is adjacent to the shaft. The BDP (140) moves in response to movement of the BPP(120). The BDP may be configured to move omni-directionally i.e. in any radial direction while the shaft is rotationally fixed. BDP is preferably configured to move in any radial direction (about 360° with respect to central longitudinal axis (A'-A) of the shaft part) while the shaft is axially-rotationally fixed. Movement of BDP in different radial directions and to different bending degrees results in a corresponding change in radial direction and/or degree of bending of the BDP (140). The BDP (140) may comprise a plurality tandemly arranged joints and is configured to bend in a curve. The BDP (140) may be configured to bend around one or more tandemly arranged joints (e.g. ball and socket joints) each having 2 DOF. The BDP (140) may be configured to bend around two or more tandemly arranged joints (e.g. revolute joints offset by 90 deg) each having 1 DOF. The BDP (140) may be configured to bend along a curve.

The steerable instrument may contain a motion amplifier region having a plane section larger than that of the BDP (140). In the motion amplifier region, consecutive plane sections gradually increase in size in the distal to the proximal direction. The motion amplifier region may be located within the shaft, or at least partially within the BPP. With the amplifier, movement of the connection and hence of the BPP results in a correspondingly larger movement of the BDP (140). Bending degree of the bendable distal part responsive to bending degree of the bendable proximal part is amplified by the motion amplifier region. An example of a motion amplifier region is set out in WO 2016/091858 A1 which is incorporated herein by reference. Advantageously, the presence of a motion amplifier region reduces the movement volume of the robotic arm and hence reduces a risk of collision with objects including adjacent equipment and additional robotic arms.

The steerable instrument is configured for rotation of the distal tip of the BDP (140) or the end effector (300) about its own axis when the BDP (140) is in a bent position, by a complementary rotation of the BPP (110). The rotation refers to axial rotation. See arrows ($r_1$ and $r_2$ in FIG. 11B). It is noted that the rotor unit (400) rotates (R) independent of rotations of the BDP (140) and BPP (120). It is appreciated that the distal tip of the BDP (140) refers in this context to the distal terminal end of the BDP.

The end effector (300) may be rotationally fixed in relation to the BDP, and the end effector (300) is rotatable when the BDP is in a bent position, by a complementary rotation of the BPP. The rotation refers to axial rotation. The end effector (300) may be directly attached to the distal end of the BDP (without a coupling).

The end effector (300) may be dismountable, in which case the BDP is provided with a coupling for attachment to the end effector (300). The coupling may be rotationally fixed in relation to the BDP, and the coupling is rotatable when the BDP is in a bent position, by a complementary rotation of the BPP. The rotation refers to axial rotation. The end effector (300) to the coupling is rotationally fixed in relation to the BDP.

Rotationally fixing the coupling or end effector (300) relative to the BDP may be achieved using a permanent (non-adjustable) connection or joint, or by means of a lockable element configured to allow rotational adjustment of and to rotationally fix the coupling or end effector in rotational relation to the BDP.

The combination of movements of the steerable instrument facilitates a rotation of BPP at its tip or of the stapler head while the BPP is in a bent position that is transmitted via a rotation of the shaft to the BDP that causes rotation of the BDP tip or stapler head while the BDP is in a bent position. With such rotation of the tip or of the stapler head, the direction of the bending plane can be maintained constant.

The combination of the movement of steerable instrument further facilitates a change in direction of the BDP tip or stapler head while the shaft is in a fixed rotational position. With such movement, the bending plane rotates around the shaft central longitudinal axis (A-A') while the shaft itself does not rotate.

To control the BDP responsive to movements of the BPP, steering wires which are known as longitudinal members (LMs) are provided. The LM controls the BDP by pulling or pushing. The steerable instrument comprises a set of longitudinal members (LM) each having a proximal end and a distal end, arranged in a longitudinal direction around a fictive tube. A transverse profile of at least one LM may demonstrate an anisotropic area moment of inertia; the transverse profile of the LM may have a square, rectangular, serif letter "I", or circular segment profile, optionally wherein one or more of the profile corners are pointed or rounded-off. The transverse profile refers to a cross-sectional profile perpendicular to an axial (A-A') direction. The LMs may be cut from a tube or provided as separate strands. With this arrangement, the tip (distal terminal end) of the BDP moves with equal ease in any direction i.e. there is no singularity. The movement response is proportion to the degree of actuation. An example of a transmission mechanism has been described in WO 2009/098244.

The BPP and BDP may each be provided with one or a plurality of tandemly arranged pivoting joints. The pivoting joints may be formed by a set of longitudinal member (LM) guides present in each of the BPP and BDP. An LM guide comprises a body having a proximal side, a distal side and an outside edge, wherein the body of the LM guide comprises a set of channels arranged around a fictive tube. Each channel passes from the proximal side to the distal side of the body. Each channel is configured to retain an LM of a set of LMs in a fixed radial position around the fictive tube. Each channel thus constrains radial movement of a set of LM. Each channel may further be configured to provide a discrete constraining point to axially rotationally constrain an LM. A channel may have a transverse profile complementary to that of the LM. A channel may have a circular transverse profile. A channel may have a rectangular transverse profile. At least one or two of the LM guides in the set may be articulated LM guides tandemly arranged and are mutually articulated, thereby supporting bending of the LMs in the BPP and BDP. An example of an LM guide (402) that is an articulated LM guide (405) is depicted in FIG. 14. The number of articulated LM guides in the BPP may be at least 1 or 2 (e.g. 2, 3, 4, 5, 6, 7, 8 or more), preferably at least 5; where there is at least 2, the BPP may bend along a curve. The number of articulated LM guides in the BDP may be at least 1 or 2 (e.g. 2, 3, 4, 5, 6, 7, 8 or more), preferably at least 5; where there are at least 2 LM guides, the BDP may bend along a curve. The articulated LM guides are in pairwise mutual contact through a pivot joint. The pivot joint may comprise a ball and socket joint, a flexible part, such as a rubber or silicone element, or a stack of spherical bodies. An arrangement of LMs and LM guides, and of a transmission mechanism for a steerable instrument have been described in WO 2016/030457 and WO 2016/091856, and are incorporated by reference herein.

In an alternative arrangement, the BPP and BDP may each be provided with a sleeve containing a plurality of arc shaped discrete slits each provided essentially perpendicular to a longitudinal axis of the BPP or BDP. Each slit may span an angle of around 150 to 210 deg. Advancing along the BPP or BDP, an orientation of a slit may change with respect to a previous slit. Preferably, each slit spans an angle of around 180 deg, and the orientation alternates between 0 and 180 deg advancing along the BPP or BDP. The sleeve supports to the LMs, while the slits allow bending of the BPP or BDP in any direction.

The steerable instrument may be that described in, for instance, WO 2009/098244, WO 2016/030457, WO 2016/091857, WO 2016/091858.

The minimally invasive instrument typically, but not necessarily enters the body via a trocar—a tube-like port inserted into an incision. The trocar is configured to receive the shaft of the steerable instrument; it is provided with a trocar passage into which the steerable instrument can axially slide and rotate, to support the steerable instrument allowing axial (A-A') displacements and also to provide a fulcrum point to change direction of the steerable instrument. A trocar is known in the art. Where the trocar can pivot freely around the incision, so the steerable instrument can pivot around the fulcrum zone in concert with the trocar.

The steerable instrument may comprise a first and second BPP tandemly arranged and that controls movement of a first and second BDP respectively tandemly arranged, as described for instance in WO 2009/098244 (see FIGS. 13A and 13B therein). In such case, the connector attached to the outer most (first) BPP controls movement of the outer most (first) BDP in the same way as described herein, and is attachable to a robotic arm. The second (inner most) BPP controls movement of the second (inner most) BDP; once the desired position of second (inner most) BDP is met, the position of the second (inner most) BPP is locked using an external clamp. Alternatively, the position of second (inner most) BPP may be controlled using an index mechanism that allows selection from a plurality of fixed discrete positions.

A robotic arm comprises a base end, an effector end and a plurality of intervening linkages connected by joints, wherein the arrangement of links and joints provides at least 6 degrees of freedom of movement to the effector end. The joints are actuatable, typically by motors, hydraulics, or pneumatics allowing control of the position and direction of the effector end by electronic signals. Each joint, also known as a kinematic pair, may offer 1 or 2 degrees of freedom (DOF) of movement, preferably 1 DOF. A joint may be a revolute or prismatic joint. A revolute joint has one degree of freedom of movement that is rotational. A prismatic joint has one degree of freedom of movement that is a linear displacement i.e. slidable. Typically a robotic arm comprises 6 joints each having 1 DOF to generate 6 DOF of movement to the effector end. Where a robot arm contains more than 6 joints, the position and direction of the effector can be attained using a plurality of different combinations of joint positions, offering redundancy that is useful for instance where the path of the robotic arm is restricted.

When the last joint is mentioned herein, it refers to the joint that is a kinematic pair of the kinematic chain at the effector end that would attach to the fitting. The last two joints refer to (1) the last joint and (2) the joint that is a kinematic pair of the kinematic chain attached to the last joint and disposed towards the base end of the robotic arm. The last three joints refer to (1) the last joint and (2) the joint that is a kinematic pair of the kinematic chain attached to the last joint and disposed towards the base end of the robotic arm, and (3) the joint that is a kinematic pair of the kinematic chain attached to joint (2) and disposed towards the base end of the robotic arm. The joints include any integrated into a robotic arm unit, and any joints added by way of an adapter added to the effector end of the robotic arm unit.

The robotic arm may be commercially provided, for instance, as manufactured by Kuka, Fanuc, ABB or may be an adapted commercially available robotic arm. An adaptation to an existing robotic arm includes, for instance, a replacement of one or more joints or linkage, or an addition of one or more controllably degrees of freedom using an adapter attached to the effector end thereby creating a new effector end.

The effector end is provided with a fitting for dismountable attachment to the connector. The fitting may be a standard fitting such as already provided by the robotic arm, or may be customised according to the parameters of the connector.

A moveable member may be provided, wherein the base end (230) of the robot arm (200) is attached to the moveable member, and wherein the position of the moveable member is adjustable (displaceable in 1 or more directions), and optionally the angle of the moveable member is adjustable (rotatable in 1 or more directions).

The moveable member is comprised in a (motorised) gantry, a (motorised) trolley, or a further robotic arm.

Further provided herein is a system comprising:
the tool as described herein, and
the stator unit as defined herein.

The system may further comprise a robotic arm as described herein. The stator unit (500) may be disposed at an effector end of the robotic arm.

The invention claimed is:
1. A system comprising:
a tool (50) comprising:
an instrument (100, 102) having a proximal end (20) and a distal (40) end comprising a shaft (130), the instrument (100, 102) provided with an end effector (300) at the distal end (40) actuated by torque,
a drive shaft (402), at least partially flexible for transfer of torque from the proximal end (20) to the end effector (300), disposed in a lumen of the instrument (100),
a rotor unit (400) comprising a body (410) disposed at the proximal end (20) of the instrument (100, 102) connected to the drive shaft (402), and that rotates around an axis of rotation (210) relative to the proximal end (20) of the instrument (100, 102), and
a stator unit (500) configured to induce rotation of the body (410) around the axis of rotation (210),
wherein
the body (410) of the rotor unit (400) is configured for dismountable engagement with a stator unit (500),
the body (410) of the rotor unit (400) is disposed with at least two cammed regions each configured to receive radial force from the stator unit (500) that induces rotation of the body (410) around the axis of rotation, and
the stator unit (500) comprises a plurality of stator pushers (530-Ua, 530-Va, 530-Wa, 530-Ub, 530-Vb, 530-Wb, 530-Uc, 530-Vc, 530-Wc) configured for movement in a direction radial to a centre of rotation (405) of the body (410) of the rotor unit (400) and for the application of the radial force.

2. The system according to claim 1, wherein the tool (50) further comprises a connector (110) rotationally fixed in relation to the proximal end of the instrument (100, 102), and the stator unit (500) comprises a complementary fitting, wherein the connector (110) is configured for dismountable attachment of the instrument (100, 102) in fixed relation to the stator unit (500) via the complementary fitting thereon.

3. The system according to claim 2 wherein the connector (110) comprises a collar having a polygonal profile.

4. The system according to claim 1, wherein the rotor unit (400) further comprises a plurality of rotor pushers (430-Ub, 430-Vb, 430-Wb), each rotor pusher is configured for movement in a direction radial to a centre of rotation of the body (410), and for receiving rotation-inducing force from the stator unit (500) and transferring it to the body (410) as the radial force.

5. The system according to claim 1, wherein the rotor pushers (430-Ub, 430-Vb, 430-Wb) are enclosed by a sterile barrier or drape (600).

6. The system according to claim 1, wherein the instrument (100) is a steerable instrument (102) comprising a bendable proximal part (120) and a bendable distal part (140) disposed either side of the shaft, the steerable instrument (100) configured such that the bendable distal part (140) bends responsive to bending of the bendable proximal part (120).

7. The system according to claim 6 where the end effector (300) is attached in fixed rotational relation to the bendable distal part (140) wherein the end effector (300) is axially rotatable when the bendable distal part (140) is in a bent position by a complementary axial rotation of the bendable proximal part (120).

8. The system according to claim 1, wherein the stator pushers (530-Ua, 530-Va, 530-Wa, 530-Ub, 530-Vb, 530-Wb, 530-Uc, 530-Vc, 530-Wc) are disposed evenly around a central point, where an axis of movement of the stator pushers coincide.

9. The system according to claim 1, wherein the stator unit (500) further comprises a ring cam (550) having an inner surface comprising at least one cammed region, configured such that rotation of the ring cam (550) induces movement of the stator pushers (530-Ua, 530-Va, 530-Wa, 530-Ub, 530-Vb, 530-Wb, 530-Uc, 530-Vc, 530-Wc) for inducing rotation of the body (410) around the axis of rotation(210).

10. The system according to claim 1, wherein a set of the plurality of stator pushers is defined as a set of phase-shifted stator pushers, PSSP, wherein the cycles of movement of the pushers within the set of PSSP have that are mutually shifted.

11. The system according to claim 1 further comprising a robotic arm, and the stator unit (500) is attached at an effector end of the robotic arm.

12. The system according to claim 1 further comprising a detachable handle, and the stator unit (500) is integrated into a handle.

13. A tool (50) as defined in claim 1 configured for dismountable engagement with a stator unit (500).

14. A stator unit (500) as defined in claim 1 configured for dismountable engagement with a tool (50).

15. A use of a tool as defined in claim 1 for dismountable engagement with a stator unit (500).

* * * * *